United States Patent [19]
Kukolja et al.

[11] 3,960,851

[45] June 1, 1976

[54] PREPARATION OF DESACETOXY-CEPHALOSPORIN SULFOXIDES FROM PENICILLIN SULFOXIDES

[75] Inventors: Stjephan P. Kukolja, Indianapolis; Steven R. Lammert, Greenwood, both of Ind.

[73] Assignee: Eli Lilly and Company, Indianapolis, Ind.

[22] Filed: July 11, 1974

[21] Appl. No.: 487,681

Related U.S. Application Data

[62] Division of Ser. No. 253,385, May 15, 1972, Pat. No. 3,843,682.

[52] U.S. Cl. .............................. 260/243 C; 424/246
[51] Int. Cl.$^2$ ........................................ C07D 501/10
[58] Field of Search ................................. 260/243 C

[56] References Cited
UNITED STATES PATENTS

| | | | |
|---|---|---|---|
| 3,819,622 | 6/1974 | Cowley et al. | 260/243 C |
| 3,843,637 | 10/1974 | Rubinfeld et al. | 260/243 C |

*Primary Examiner*—Nicholas S. Rizzo
*Attorney, Agent, or Firm*—William C. Martens, Jr.; Everet F. Smith

[57] ABSTRACT

A penicillin sulfoxide ester is reacted with sulfuryl chloride at a temperature of from about 75°C. to about 120°C. to produce a novel 2-chlorosulfinyl-azetidin-4-one intermediate, which intermediate is treated with an alkaline reagent to produce a desaceetoxycephalosporin sulfoxide.

6 Claims, No Drawings

PREPARATION OF DESACETOXY-CEPHALOSPORIN SULFOXIDES FROM PENICILLIN SULFOXIDES

This is a division of application Ser. No. 253,385, filed May 15, 1972 now U.S. Pat. No. 3,843,682.

BACKGROUND OF THE INVENTION

The semi-synthetic production of a desacetoxycephalosporin antibiotic by ring expansion of a penicillin starting material has been important since the advent of the invention by Morin and Jackson (U.S. Pat. No. 3,275,626) who describe and claim a process for converting a penicillin sulfoxide ester to an ester of a desacetoxycephalosporin. Several and varied improvements have been made upon this Morin-Jackson process (see, for example, British Pat. No. 1,204,972; British Pat. No. 1,204,394; and U.S. Pat. No. 3,591,585).

The mechanism which is postulated in U.S. Pat. No. 3,275,626 for the ring expansion of the penicillin sulfoxide ester to an ester of a desacetoxycephalosporin is by scission of the $S-C_2$ bond to form a sulfenic acid intermediate. This mechanism has now been established conclusively (see R. D. G. Cooper, J.A.C.S., 92, (1970) pp. 5010–5011). The sulfenic acid intermediate is then ring-closed to produce the ester of a desacetoxycephalosporin.

It has now been found to be possible to effect a ring expansion of a penicillin sulfoxide ester to produce therefrom a desacetoxycephalosporin sulfoxide ester. In accordance with known techniques, such sulfoxide can be readily converted to an active cephalosporin antibiotic by reduction of the sulfoxide group and cleavage of the ester function to produce the free acid or a pharmaceutically acceptable salt thereof.

SUMMARY OF THE INVENTION

It is an object of this invention therefore to provide a process for preparing a desacetoxycephalosporin sulfoxide which comprises reacting a penicillin sulfoxide having the formula

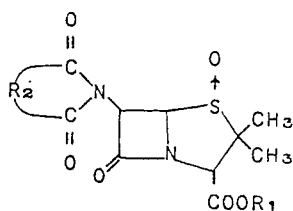

with from about 0.9 to about 1.5 moles of sulfuryl chloride per mole of the penicillin sulfoxide at a temperature of from about 75°C. to about 120°C. to produce a sulfinyl chloride having the formula

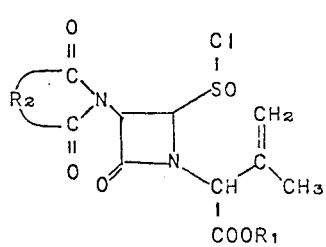

and reacting the resulting sulfinyl chloride with at least an equimolar amount of a tertiary amine to produce a desacetoxycephalosporin sulfoxide having the formula

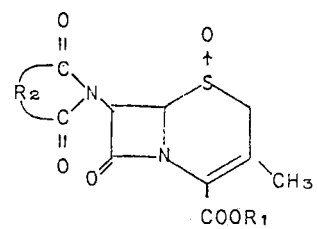

in which, in the above formulae, $R_1$ is the residue of an ester group which is removable by hydrogenation or acid treatment; and $R_2$ is the residue of an imide derived from a dicarboxylic acid.

Another object of this invention relates to novel stable sulfinyl chlorides having the formula

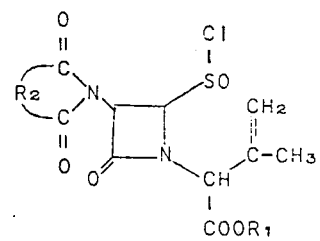

in which $R_1$ is the residue of an ester group which is removable by hydrogenation or acid treatment; and $R_2$ is the residue of an imide derived from a dicarboxylic acid.

DETAILED DESCRIPTION OF THE INVENTION

As delineated hereinabove, the novel stable sulfinyl chlorides of this invention have the formula

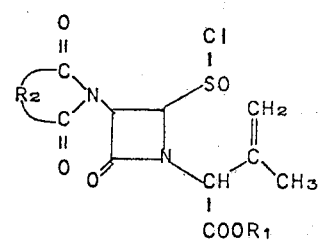

$R_1$ is the above formula denotes a carboxy protecting group which is the residue of an ester function and which is removable by acid treatment or by hydrogenation. Preferred carboxy protecting groups include, for example, $C_1$–$C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2$–$C_6$ alkanoyloxymethyl, phenacyl, or p-halophenacyl, in any of the above of which halo denotes chlorine, bromine or iodine.

Specific illustrations of the preferred ester residues of the carboxyl group of the sulfinyl chlorides of this invention include, for example, methyl, ethyl, n-propyl, isopropyl, n-butyl, sec-butyl, isobutyl, t-butyl, 2,2,2-trichloroethyl, 2,2,2-tribromoethyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, p-chlorophenacyl, p-bromophenacyl, and the like.

Highly preferred ester residues are methyl, benzyl, p-nitrobenzyl, p-methoxybenzyl, benzhydryl, and 2,2,2-trichloroethyl. The cyclic imide radical, defined by $R_2$ taken together with the nitrogen-carbonyl combination to which it is bonded, can be formed by reacting the 6-amino group of 6-aminopenicillanic acid (6-APA) or an ester of 6-APA with a dicarboxylic acid or anhydride or other reactive variant thereof, followed by reacting the resulting derivative with a $C_1$ to $C_4$ alkyl haloformate, for example, ethyl chloroformate, in the presence of an organic base. Preferably, $R_2$ is $C_2$–$C_4$ alkylene, 1,2-cyclohexylene, 1,2-phenylene, 1,2-cyclohexenylene, or a substituted derivative of any of these having from 1 to 4 substituents selected from the group consisting of $C_1$–$C_3$ alkyl, $C_1$–$C_3$ alkoxy, nitro, fluoro, chloro, bromo and iodo. Typically, $R_2$ is the residue of a $C_4$ to $C_{10}$ dicarboxylic acid, and the cyclic imide thus represented is prepared from such dicarboxylic acid, its anhydride, or an appropriate reactive variant thereof. Cyclic imides can be prepared, for example, from acids such as succinic, maleic, glutaric, diglycolic, phthalic, and the like, or their respective anhydrides, as well as from cyclohexane1,2-dicarboxylic, 3-cyclohexene-1,2-dicarboxylic, halogen substituted dicarboxylic acids or anhydrides such as 4,5-dichlorophthalic, tetraiodophthalic, 4-bromophthalic, nitro substituted dicarboxylic acids and anhydrides such as 3-nitrophthalic acid, alkyl substituted dicarboxylic acids and anhydrides such as methylmaleic acid, as well as related compounds and compounds of similar reactivities. Additional examples of cyclic anhydrides of the type defined are found in the prior art such as in the *Journal of Organic Chemistry*, Volume 26, pp. 3365–3367 (September, 1961). 6-Phthalimidopenicillanic acid can also be prepared from 6-APA and N-carboethoxyphthalimide according to the procedure of Y. G. Perron et al., *Journal of Medicinal Chemistry*, Volume 5, (1962), p. 1016.

The novel sulfinyl chlorides of this invention are useful as intermediates in the production of cephalosporin sulfoxides and are prepared from penicillin sulfoxides during the course of the process of this invention. The sulfinyl chlorides result from the interaction of a penicillin sulfoxide ester with sulfuryl chloride at an elevated temperature. The reaction is carried out by mixing from about 0.9 to about 1.5 moles, and preferably, about 1.0 to about 1.1 moles, of sulfuryl chloride with each mole of the penicillin sulfoxide ester. The resulting mixture, preferably dissolved in a suitable inert solvent, is heated to a temperature of from about 75°C. to about 120°C. Suitable solvents are those having a boiling point at least as high as the temperature of reaction and include, for example, aromatic hydrocarbons such as benzene and toluene; halogenated hydrocarbons such as carbon tetrachloride, chlorobenzene, bromoform, bromobenzene, ethylene dichloride, ethylene dibromide, and the like; amides, such as dimethylformamide, dimethylacetamide, and the like; aliphatic nitriles, such as acetonitrile, propionitrile, and the like; esters, such as ethyl acetate, and the like; ethers, such as dioxane, and the like; and any other appropriate inert solvents. Preferred solvents are those having a boiling point within the range of the temperature at which the reaction is to be carried out, thereby permitting the reaction mixture to be refluxed while retaining temperature control.

The resulting reaction mixture generally is heated at a temperature in the defined range for a period of from about 0.5 to about 4 hours after which time the stable sulfinyl chloride intermediate is isolated from the reaction mixture, typically by evaporating the reaction mixture in vacuo to remove solvent and any excess sulfuryl chloride.

Examples of sulfinyl chlorides of this invention include:

2-chlorosulfinyl-3-phthalimido-1-(1′-methoxycarbonyl-2′-methylprop-2′-enyl)acetidin-4-one;

2-chlorosulfinyl-3-phthalimido-1-[1′-(2″,2″,2″-trichloroethoxycarbonyl)-2′-methylprop-2′-enyl]azetidin-4-one;

2-chlorosulfinyl-3-phthalimido-1-[1′-(p-nitrobenzyloxycarbonyl)-2′-methylprop-2′-enyl]azetidin-4-one;

2-chlorosulfinyl-3-succinimido-1-(1′-benzyloxycarbonyl-2′-methylprop-2′-enyl)azetidin-4-one;

2-chlorosulfinyl-3-phthalimido-1-(1′-benzhydryloxycarbonyl-2′-methylprop-2′-enyl)azetidin-4-one;

2-chlorosulfinyl-3-glutarimido-1-[1′-(t-butoxycarbonyl)-2′-methylprop-2′-enyl]azetidin-4-one;

2-chlorosulfinyl-3-diglycolimido-1-[1′-(p-nitrobenzyloxycarbonyl)-2′-methylprop-2′-enyl]azetidin-4-one;

2-chlorosulfinyl-3-(3′-bromophthalimido)-1-(1′-benzhydryloxycarbonyl-2′-methylprop-2′-enyl)azetidin-4-one;

2-chlorosulfinyl-3-tetraiodophthalimido-1-[1′-(p-nitrobenzyloxycarbonyl)-2′-methylprop-2′-enyl]azetidin-4-one;

2-chlorosulfinyl-3-(3′-nitrophthalimido)-1-[1′-(p-methoxybenzyloxycarbonyl)-2′-methylprop-2′-enyl]azetidin-4-one;

2-chlorosulfinyl-3-(4′,5′-dichlorophthalimido)-1-(1′-phthalimidomethoxycarbonyl-2′-methylprop-2′-enyl)azetidin-4-one;

2-chlorosulfinyl-3-hexahydrophthalimido-1-(1′-succinimidomethoxycarbonyl-2′-methylprop-2′-enyl)azetidin-4-one;

2-chlorosulfinyl-3-diglycolimido-1-[1′-(2′-iodoethoxycarbonyl)-2′-methylprop-2′-enyl]azetidin-4-one;

2-chlorosulfinyl-3-(1′,2′,3′,6′-tetrahydrophthalimido)-1-(1′-pivaloyloxymethoxycarbonyl-2′-methylprop-2′-enyl)azetidin-4-one;

2-chlorosulfinyl-3-(3′-methylphthalimido)-1-(1′-acetoxymethoxycarbonyl-2′-methylprop-2′-enyl)azetidin-4-one;

2-chlorosulfinyl-3-(4′-methoxyphthalimido)-1-(1′-phenacyloxycarbonyl-2′-methylprop-2′-enyl)azetidin-4-one;

2-chlorosulfinyl-3-methylmalonimido-1-[1′-nitrobenzyloxycarbonyl-2′-methylprop-2′-enyl]azetidin-4-one;

2-chlorosulfinyl-3-glutarimido-1-[1′-(p-chlorophenacyloxycarbonyl)-2′-methylprop-2′-enyl]azetidin-4-one;

2-chlorosulfinyl-3-(3′-isopropylphthalimido)-1-[1′-(2″,2″,2″-trichloroethoxycarbonyl)-2′-methylprop-2′-enyl]azetidin-4-one;

2-chlorosulfinyl-3-(3′-fluorophthalimido)-1-[1′-(p-methoxybenzyloxycarbonyl)-2′-methylprop-2′-enyl]azetidin-4-one;

2-chlorosulfinyl-3-(1',4',5',6'-tetrahydrophthalimido)-1-[1'-(p-nitrobenzyloxycarbonyl)-2'-methylprop-2'-enyl]-azetidin-4-one;

and the like.

The second step of the process of this invention involves the ring-closure conversion of the sulfinyl chloride intermediate produced from the first step of the process. The sulfinyl chloride intermediate, upon subjection to alkaline conditions, achieves such ring-closure. Cyclization of the sulfinyl chloride to the desacetoxycephem is believed to proceed by initial abstraction of the α-proton which results in increasing the nucleophilicity of the double bond. Concomitantly, the activated sulfinyl group undergoes nucleophilic substitution resulting in formation of the S-C bond and ring-closure to the six-membered system. Alkaline reagents which are suitable for achieving the cyclization of the sulfinyl chloride structure to produce a 3-cephem ring system include tertiary amines and mild inorganic alkaline reagents. Examples of suitable tertiary amines include those which contain alkyl groups having from 1 to 5 carbon atoms, such as trimethylamine, triethylamine, tripropylamine, tributylamine, triamylamine, methyldiethylamine, and the like. Suitable typical inorganic alkaline reagents are salts of a strong base and a weak acid such as sodium carbonate, sodium bicarbonate, sodium acetate, potassium carbonate, potassium bicarbonate, potassium acetate, lithium carbonate, lithium bicarbonate, lithium acetate, disodium hydrogen phosphate, trisodium phosphate, dipotassium hydrogen phosphate, tripotassium phosphate, sodium benzoate, potassium benzoate, sodium formate, potassium formate, disodium phthalate, potassium hydrogen phthalate, and the like.

Typically, the ring-closure step of the process of this invention is accomplished by mixing the sulfinyl chloride and the alkaline reagent in an appropriate solvent. The subjecting of the sulfinyl chloride intermediate to an alkaline medium brings about a ring-closure with effective elimination of HCl. The purpose of a solvent is merely to facilitate mixing of the reactants. Therefore, any solvent which is inert to the reactants can be employed. Any of the solvents mentioned hereinabove for use in the sulfuryl chloride reaction are available for use in the ring-closure step. Indeed, since the temperature limitations of the first step of the process of this invention do not apply in the ring-closure step, many lower boiling solvents, such as chloroform, methylene chloride, and the like, also can be employed.

The temperature at which the ring-closure is carried out is not critical. Generally, ring-closure will be achieved at a temperature of from about 10°C. to about 50°C., and, preferably, at from about 20°C. to about 30°C.

The alkaline reagent which is employed must be present in an amount at least equimolar to the sulfinyl chloride intermediate. Generally, a slight excess of the alkaline reagent will be employed, typically on a basis of about 1.1 to about 1.5 moles of the base per mole of the sulfinyl chloride.

The ring-closure reaction is quite rapid and will be completed within a period extending from about 5 minutes to about 2 hours. The cephalosporin sulfoxide product can be isolated using techniques well known in the art. For example, the product can be recovered from the reaction mixture by evaporating the solvent and any excess tertiary amine which may be present. The residue which contains product and amine hydrochloride or an inorganic salt is then mixed with an organic solvent, such as ethyl acetate, which selectively dissolves the cephalosporin sulfoxide product. The dissolved product can then be further purified by common techniques, such as, for example, recrystallization or gradient elution.

It is not essential that the sulfinyl chloride be isolated from its reaction mixture prior to ring-closure to form the cephalosporin sulfoxide. The sulfinyl chloride can remain in the reaction mixture in which it was formed, and the alkaline reagent can then be added thereto. Generally, in such an instance, a sufficient excess of alkaline reagent will be employed to decompose any excess sulfuryl chloride which may be present.

The desacetoxycephalosporin sulfoxide ester produced in accordance with the provisions of this invention can be converted by known techniques to an active antibiotic by cleavage of the ester function and reduction of the sulfoxide to the corresponding desacetoxycephalosporin. Deesterification can be achieved by treatment of the ester with an acid such as trifluoroacetic acid, hydrochloric acid, and the like, or with zinc and acid, such as formic acid, acetic acid or hydrochloric acid. It can likewise be accomplished by hydrogenating the ester in the presence of palladium, rhodium or a compound thereof, in suspension or on a carrier such as barium sulfate, carbon, alumina, or the like. Reduction of the sulfoxide group to the sulfide can be achieved in accordance with the process defined in U.S. Pat. No. 3,641,014. Furthermore, the substituent which is present in the 7-position of the desacetoxycephalosporin sulfoxide can be cleaved in accordance with known techniques and replaced with other functional groups to produce a wide variety of active antibiotic compounds.

This invention is further illustrated by reference to the examples which follow. It is not intended that this invention be limited in scope by reason of any of the examples provided herein.

EXAMPLE I

A. Preparation of Sulfinyl Chloride

A solution of 1.496 g. (4 mmol.) of methyl 6-phthalimido-2,2-dimethylpenam-3-carboxylate-1-oxide and 0.36 ml. (4.4 mmol.) of sulfuryl chloride in 80 ml. of dry carbon tetrachloride was refluxed for 50 minutes. The reaction mixture was cooled and evaporated to dryness under vacuum. An NMR spectrum of the resulting crude product was consistent with the structure of 2-chlorosulfinyl-3-phthalimido-1-(1'-methoxycarbonyl-2'-methylprop-2'-enyl)azetidin-4-one; 118 (broad $s$, 3), 231 ($s$, 3), 304 (broad $s$, 2), 312 ($d$, $l$, J = 2 Hz), 346 ($d$, $l$, J = 4 Hz, beta-lactam 2-H), 354 ($d$, $l$, J = 4 Hz, beta-lactam 3-H), and 470 Hz ($m$, 4, aromatic H). IR (CHCl$_3$) 1790 (beta-lactam carbonyl), and 1075 and 1086 cm.$^{-1}$ (—S=O). A noncrystalline analytical sample was prepared by extraction of the crude product with cold diethyl ether. Evaporation of the filtered ethereal solution gave a white foam.

Analysis, Calculated for $C_{17}H_{15}N_2O_6SCl$: C, 49.70; H, 3.68; N, 6.82; O, 23.37. Found: C, 49.42; H, 3.68; N, 6.91; O, 23.31.

B. Ring-Closure of the Sulfinyl Chloride

To a solution of the crude sulfinyl chloride obtained from Part A above in 50 ml. of dry methylene chloride was added dropwise 0.56 ml. (4 mmol.) of triethylamine in 7 ml. of methylene chloride. The reaction mixture was stirred for 20 minutes at room temperature and then evaporated in vacuo to dryness. The residue was dissolved in 20 ml. of ethyl acetate, filtered to remove triethylamine hydrochloride, and the filtrate was evaporated in vacuo to a tan foam. Filtration chromatography on 15 g. of silica gel using a 4:1 mixture of benzene and ethyl acetate gave 630 mg. of an impure product which was recrystallized from acetone to give 430 mg. (29%) of methyl 7-phthalimido-3-methyl-3-cephem-4-carboxylate-1-oxide (m.p. 215°C.). All physical and chemical data of this compound agreed with that of the authentic sulfoxide prepared by oxidation of methyl 7-phthalimido-3-methyl-3-cephem-4-carboxylate.

EXAMPLE II

A. Preparation of the Sulfinyl Chloride

A solution of 2.48 g. (5.0 mmol.) of p-nitrobenzyl 6-phthalimido-2,2-dimethylpenam-3-carboxylate-1-oxide and 0.45 ml. (5.5 mmol.) of sulfuryl chloride in 150 ml. of dry benzene was refluxed for 55 minutes. The reaction mixture was cooled and evaporated in vacuo to a yellow foam. An NMR ($CDCl_3$) of the crude product showed the major component to be 2-chlorosulfinyl-3-phthalimido-1-[1'(p-nitrobenzyloxycarbonyl)-2'-methylprop-2'-enyl]azetidin-4-one: 118 (3, $s$, olefinic $CH_3$); 305 ($l$, $s$); 325 (2, $s$, p-nitrobenzyl methylene); 344 ($l$, $d$, J = 5 Hz, beta-lactam H); 357 ($l$, $d$, J = 5 Hz, beta-lactam H); 473 (4, $m$, phthalimido aromatic H) and 475 Hz (4, AB$q$, T = 19 and 8 Hz, p-nitrobenzyl aromatic H).

B. Ring-Closure of the Sulfinyl Chloride

The crude sulfinyl chloride obtained from Part A above was dissolved in 150 ml. of dry benzene, and 0.75 ml. (5 mmol.) of triethylamine was added dropwise at room temperature. The resulting reaction mixture was stirred at room temperature for about 1.5 hours and then evaporated to dryness. The residue was taken up in 60 ml. of ethyl acetate, washed twice with 50 ml. of water, then with 50 ml. of brine, and dried over magnesium sulfate. The ethyl acetate solution was evaporated in vacuo to dryness to give a light brown amorphous solid which was chromatographed on a 2.5 × 25 cm. silica gel column developed with 1500 ml. of 10 percent ethyl acetate in benzene, 1500 ml. of 20 percent ethyl acetate in benzene, and 1000 ml. of 25 percent ethyl acetate in benzene. Fractions of 18–20 ml. each were taken every 16 minutes. Fractions 145–214, when evaporated, gave 730 mg. of p-nitrobenzyl 7-phthalimido-3-methyl- 3-cephem-4-carboxylate-1-oxide. Recrystallization from ethyl acetate gave 640 mg. (26%) of tan crystals.

NMR ($CDCL_3$) 132 (3, $s$, 3-methyl), 239 (2, AB$q$, J = 15 and 16 Hz, 2-$CH_2$); 299 ($l$, $d$, J = 5 Hz, beta-lactam H); 328 (2, $s$, p-nitrobenzyl methylene); 377 ($l$, $d$, J = 5 Hz, beta-lactam H); 477 (4, $m$, phthalimido aromatic H); and 479 Hz (4, AB$q$, J = 15 and 9 Hz).

MS: M$^+$, 495.

Analysis, Calculated for $C_{23}H_{17}N_3O_8S$: C, 55.76; H, 3.46; N, 8.48; O, 25.83; S, 6.47. Found: C, 55.63; H, 3.67; N, 8.73; O, 26.00; S, 6.71.

We claim:

1. A process for preparing a desacetoxycephalosporin sulfoxide which comprises reacting a penicillin sulfoxide having the formula

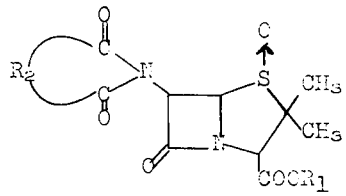

with from about 0.9 to about 1.5 moles of sulfuryl chloride per mole of the penicillin sulfoxide at a temperature of from about 75°C. to about 120°C. to produce a sulfinyl chloride having the formula

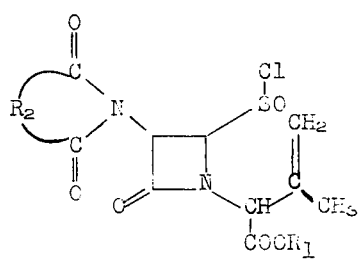

and reacting the resulting sulfinyl chloride with at least an equimolar amount of a tertiary amine containing alkyl groups having from 1 to 5 carbon atoms each to produce a desacetoxycephalosporin sulfoxide having the formula

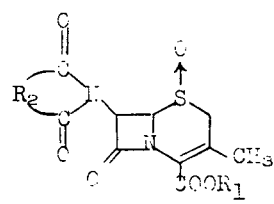

in which, in the above formulae, $R_1$ is the residue of an ester group which is removable by hydrogenation or acid treatment; and $R_2$ is the residue of an imide derived from a dicarboxylic acid.

2. Process of claim 1, in which $R_2$ is $C_2$–$C_4$ alkylene, 1,2-cyclohexylene, 1,2-phenylene, 1,2-cyclohexenylene, or a substituted derivative of any of the above having from 1 to 4 substituents selected from the group consisting of $C_1$–$C_3$ alkyl, $C_1$–$C_3$ alkoxy, nitro, fluoro, chloro, bromo, or iodo.

3. Process of claim 2, in which $R_1$ is $C_1$–$C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2$–$C_6$ alkanoyloxymethyl, phenacyl, or p-halophenacyl.

4. Process of claim 3, in which $R_2$ is 1,2-phenylene.

5. Process of claim 4, in which $R_1$ is p-nitrobenzyl.

6. Process of claim 1, in which the tertiary amine is triethylamine.

* * * * *